US012796939B2

(12) United States Patent
Barnacka et al.

(10) Patent No.: US 12,796,939 B2
(45) Date of Patent: Nov. 17, 2026

(54) SYSTEM AND METHOD FOR NONINVASIVE MONITORING, DIAGNOSIS AND REPORTING OF CARDIOVASCULAR STENOSIS

(71) Applicants: Anna Barnacka, Cambridge, MA (US); Karlen Shahinyan, Boston, MA (US)

(72) Inventors: Anna Barnacka, Cambridge, MA (US); Karlen Shahinyan, Boston, MA (US)

( * ) Notice: Subject to any disclaimer, the term of this patent is extended or adjusted under 35 U.S.C. 154(b) by 1044 days.

(21) Appl. No.: 17/590,813

(22) Filed: Feb. 1, 2022

(65) Prior Publication Data

US 2022/0240796 A1 Aug. 4, 2022

Related U.S. Application Data

(60) Provisional application No. 63/144,031, filed on Feb. 1, 2021.

(51) Int. Cl.
*A61B 5/021* (2006.01)
*A61B 5/00* (2006.01)
(Continued)

(52) U.S. Cl.
CPC ........ *A61B 5/02028* (2013.01); *A61B 5/6815* (2013.01); *A61B 5/7405* (2013.01); *G16H 10/60* (2018.01)

(58) Field of Classification Search
CPC ... A61B 5/02; A61B 5/02007; A61B 5/02028; A61B 5/6815–6817; A61B 5/7405;
(Continued)

(56) References Cited

U.S. PATENT DOCUMENTS

| | | | | |
|---|---|---|---|---|
| 9,101,274 B2 | 8/2015 | Bakema et al. | | |
| 2008/0139951 A1* | 6/2008 | Patangay | A61B 5/33 | 623/1.15 |

(Continued)

OTHER PUBLICATIONS

Hayward, James "New IDTechEx Report Addresses Key Questions About the $25bn Hearables Market." Wearable Technology Insights, Nov. 3, 2020 www.wearabletechnologyinsights.com/articles/22130/what-does-the-future-hold-for-the-hearables-market, accessed Jan. 23, 2025 (Year: 2020).*

*Primary Examiner* — Matthew Kremer
*Assistant Examiner* — Aaron Merriam
(74) *Attorney, Agent, or Firm* — John Gillis

(57) ABSTRACT

A system (CV stenosis system) and method for noninvasive cardiac stenosis monitoring, diagnosis, analysis and reporting are disclosed. The CV stenosis system includes an in-ear biosensor system and a data analysis system. The in-ear biosensor system includes at least one earbud placed at or within an ear canal of an individual, where the at least one earbud includes one or more acoustic/vibration sensors that operate in both infrasonic and audible frequency ranges and detect biosignals from the individual. The data analysis system receives the biosignals from the biosensor system, separates the biosignals into components including infrasonic cardiac signals, and determines a type and level/severity of cardiovascular stenosis of the individual based upon the biosignals. In embodiments, the CV stenosis system can detect aortic stenosis and determine its severity, and detect stenoses of the left and right carotid arteries.

12 Claims, 10 Drawing Sheets

(51) Int. Cl.

| | |
|---|---|
| ***A61B 5/02*** | (2006.01) |
| ***A61B 5/024*** | (2006.01) |
| ***A61B 5/08*** | (2006.01) |
| ***A61B 7/00*** | (2006.01) |
| ***G16H 10/60*** | (2018.01) |
| ***G16H 40/67*** | (2018.01) |
| ***G16H 80/00*** | (2018.01) |

(58) Field of Classification Search
CPC ........... A61B 5/024–02405; A61B 2562/0204; A61B 7/00; A61B 7/045; G16H 10/60; G16H 50/00–30; G16H 80/00
See application file for complete search history.

(56) References Cited

U.S. PATENT DOCUMENTS

| | | | | |
|---|---|---|---|---|
| 2012/0232427 | A1* | 9/2012 | Bakema | B06B 1/06 600/586 |
| 2016/0287166 | A1* | 10/2016 | Tran | A61B 5/74 |
| 2018/0184918 | A1* | 7/2018 | Kline | A61B 5/72 |
| 2019/0247010 | A1* | 8/2019 | Barnacka | A61B 8/02 |
| 2019/0343480 | A1* | 11/2019 | Shute | A61B 5/7203 |
| 2021/0045647 | A1 | 2/2021 | Barnacka et al. | |

* cited by examiner

ECG (v)
0.20
0.15
0.10
0.00
0.01
-0.05
501 catheter BP (mmHg)
90
80
70
60
50
401 biosignal amplitude (v)
0.2
0.1
0.0
-0.1
-0.2
101

524
biosignal amplitude (v) [ < 15 Hz ]
0.4
0.3
0.2
0.1
0.0
-0.1
-0.2
-0.3
301

202
203
total_HF_power
524
902
biosignal amplitude (v) [ > 15 Hz ]
0.02
0.01
0.00
-0.01
-0.02
LVET_HF_power -1.0
-0.5
0.0
0.5
1.0
1.5
LVET (208)
time (sec)
310

SYSTEM AND METHOD FOR NONINVASIVE MONITORING, DIAGNOSIS AND REPORTING OF CARDIOVASCULAR STENOSIS

RELATED APPLICATIONS

This application claims the benefit under 35 USC 119(e) of U.S. Provisional Application No. 63/144,031 filed on Feb. 1, 2021, which is incorporated herein by reference in its entirety.

FIELD OF THE INVENTION

The present invention generally relates to the field of noninvasive cardiovascular monitoring. In particular, the present invention is directed to a system and method for cardiovascular stenosis monitoring, diagnosis, analysis and reporting.

BACKGROUND OF THE INVENTION

Cardiovascular stenosis refers to medical conditions associated with the cardiovascular system of the individual that impede or restrict the flow of blood. Cardiovascular stenosis can cause individuals to feel week or lethargic, and can lead to serious health problems including blood clots, internal bleeding, arrhythmias, infections of the heart such as endocarditis, cardiac arrest and stroke. The most common types of cardiovascular stenoses affect heart valves and arteries of the heart, neck and kidneys. Less common stenoses affect major veins.

Cardiovascular stenosis has different types. These types include arterial stenosis, which is associated with a narrowing of arteries outside of or away from the heart that restricts blood flow through the arteries; cardiac stenosis, which is associated with damage to the valves, chambers, and major blood vessels of the heart that restricts blood flow through and out of the heart; and venous stenosis.

Arterial stenosis has multiple risk factors and causes. As individuals age, their arteries gradually lose some of their elasticity and typically become narrower over time. The narrowing is most often due to materials in the bloodstream that deposit on the inner walls of the arteries and buildup over time, also known as plaque. The plaque can narrow the arteries and thus restrict the flow of blood through the arteries. The level of plaque buildup is associated with factors including age, high blood pressure, genetic predisposition, and environmental factors including cigarette smoking history, reduced exercise level and diets higher in fat and cholesterol, in examples. The narrowing of arteries associated with arterial stenosis can also be caused by genetic abnormalities and the formation of scar tissue on the inner walls of the arteries.

The combination of plaque buildup within the arteries and the potential for scarring is especially a problem with specific arteries including the coronary, carotid and renal arteries. For this reason, stenosis of these arteries are of particular interest to medical professionals.

The heart includes chambers, major blood vessels and valves. The chambers include the left and right ventricle and the left and right atrium. The major blood vessels of the heart include the aorta, pulmonary artery, pulmonary vein, inferior vena cava and the superior vena cava. The valves include the aortic, mitral, tricuspid and pulmonary valves.

More detail for the valves and their operation is as follows. The aortic valve lies between the left ventricle and the aorta, and controls the flow of blood from the left ventricle through the aorta; the mitral valve separates the left atrium from the left ventricle; the tricuspid valve separates the right atrium from the right ventricle; and the pulmonary valve controls the flow of oxygen-rich blood from the right ventricle to the lungs.

The aorta and the pulmonary artery send oxygen-rich blood from the heart throughout the body of the individual. The aorta directs blood to all organs except the lungs, while the pulmonary artery directs blood to the lungs.

Cardiac stenosis refers to damage to or weakness of the heart valves, chambers, and/or its major blood vessels that correspondingly restricts the flow of blood through and out of the heart. This damage or weakness can be caused by one or more of: diseases including rheumatic fever; infections of the heart such as endocarditis; genetic abnormalities including bicuspid aortic valve; damage caused by medical procedures and increasing age. The medical procedures can include radiofrequency ablation of the heart to treat arrhythmias, radiation therapy, chemotherapy and catheter insertion, in examples. Aortic and carotid artery stenosis are among the most common types of cardiac stenosis and are of particular interest to medical professionals.

Operation and health of the cardiovascular system is essential to human health. For this reason, medical professionals use various medical diagnostics systems to assess cardiovascular stenosis. These existing medical diagnostics systems can be non-invasive or invasive. The non-invasive systems include an electrocardiogram system (ECG/EKG system), echocardiogram system (echo system), a sphygmomanometer (BP cuff system), and a phonocardiogram system (PCG system), in examples. Another non-invasive system is a photoplethysmography (PPG) system, but it is less accurate than the other systems and must be used in conjunction with one or more of the other systems to detect cardiovascular stenosis.

The invasive systems include catheter systems including aortic catheter systems (AO catheter). The echo system is the primary existing medical diagnostics system for assessing the severity of aortic stenosis, in one example.

SUMMARY OF THE INVENTION

Biosignals are signals in living beings such as human individuals that can be detected, observed and/or measured. Examples of biosignals from individuals include acoustic signals, pressure signals, thermal signals and electrical signals, to name a few. The acoustic signals are created as a result of breathing and physical/mechanical operations within the individual's body. These operations include blood flow throughout the cardiovascular system, and opening and closing of valves within the heart and the blood vessels, in examples. These acoustic signals can be in either the infrasonic range (infrasonic signals) or in the audible range (audible signals) or both. The pressure signals are created by pressure or tension within the body. The thermal signals are created in response to physical and biochemical processes within the body. The electrical signals are associated with changes in electrical current over time, across a specialized tissue, organ, or cell system such as the nervous system.

Infrasounds are sounds or acoustic vibrations with frequencies below the range of human hearing. The frequency range of infrasounds is between 0 and 20 Hz. Hemodynamics refers to the physical study of blood flow and the cardiovascular system through which the blood flows.

The human body is a robust infrasonic sound generator and generates infrasounds through various operations of the cardiovascular system and via musculoskeletal motion, in examples. The operations of the cardiovascular system that generate infrasound include myocardial contractions of the heart, arterial wall vibrations in response to blood flowing through the arteries, turbulence associated with the blood flow itself in arteries and veins, and heart valve operation, in examples.

The existing medical diagnostics systems have limitations. In one example, even the non-invasive versions of these systems require that the individual attend a clinical setting/doctor's office in person. The ECG system, for example, requires a trained technician or medical professional to attach and place possibly twelve or more electrodes on the individual's skin. This is time-intensive and increases cost. In another example, the systems are "one shot" systems: they monitor the cardiovascular function of the individual for only a specific period of time, typically two minutes or less. In yet other examples, the invasive versions of the medical diagnostics systems are expensive, require extended hospital stays and/or multiple clinical office visits, and have a risk of vascular or cardiac perforation, bleeding, infection and even death in some rare instances.

A cardiovascular stenosis monitoring and reporting system (CV stenosis system) is proposed. The proposed CV stenosis system can provide noninvasive detection and diagnosis of cardiovascular stenosis, while also overcoming the limitations of the existing medical diagnostics system. The proposed CV stenosis system performs monitoring of blood flow in the cardiovascular system using concepts of Infrasonic Hemodynography (IH), via low-cost earbuds of the in-ear biosensor system.

In more detail, the proposed CV stenosis system includes an in-ear biosensor system worn by an individual, and a data analysis system in communication with the in-ear biosensor system. The in-ear biosensor system includes at least one earbud placed at or within an ear canal of an individual, where the at least one earbud includes one or more infrasound/vibration sensors that detect biosignals including infrasounds indicative of blood vessel stenosis from the individual. The data analysis system receives the biosignals including the infrasounds from the biosensor system, and can characterize a level of stenosis in one or more blood vessels based upon the infrasounds indicative of blood vessel stenosis.

In general, according to one aspect, the invention features a cardiovascular stenosis monitoring, diagnosis, analysis and reporting system (CV stenosis system). The CV stenosis system comprises an interface configured to receive biosignals including infrasonic cardiac signals from one or more earbuds worn by an individual, and a data analysis system that detects and characterizes cardiovascular stenosis of the individual based upon the received biosignals.

The data analysis identifies and measures aspects of the cardiac signals using representations of a shape of the cardiac signals, and derives vital signs from the aspects of the cardiac signals. In one embodiment, the data analysis system passes the aspects of the cardiac signals, in conjunction with the vital signs and with the representations of cardiac shape, as input to one or more previously built cardiovascular stenosis models to provide a prediction and severity of aortic stenosis and a prediction of left or right carotid artery stenosis as output of the one or more models.

In one implementation, the data analysis system derives a left ventricular ejection time (LVET) vital sign and a rapid ejection period (REP) vital sign from the biosignals, divides the REP by the LVET to obtain an Ejection Efficiency Ratio, and compares the Ejection Efficiency Ratio to threshold values to detect aortic cardiovascular stenosis and characterize its severity.

In another implementation, the data analysis system calculates a left high frequency power ratio for a left cardiac signal from a left earbud and calculates a right high frequency power ratio for a right cardiac signal from a right earbud. The left high frequency power ratio relates a high frequency power calculated for an LVET of the left cardiac signal during a cardiac cycle, to a high frequency power calculated for the left cardiac signal over the cardiac cycle. In a similar vein, the right high frequency power ratio relates a high frequency power calculated for the LVET of the right cardiac signal during the cardiac cycle, to a high frequency power calculated for the right cardiac signal over the cardiac cycle.

The data analysis system then subtracts the right high frequency power ratio from the left high frequency power ratio and compares the difference to a threshold value to detect carotid artery cardiovascular stenosis and characterize it as left carotid artery cardiovascular stenosis. The data analysis system also subtracts the left high frequency power ratio from the right high frequency power ratio to obtain a second difference, and compares the second difference to the threshold value to detect carotid artery cardiovascular stenosis and characterize it as right carotid artery cardiovascular stenosis.

In yet another implementation, the data analysis system concludes that left carotid artery stenosis is present when the left high frequency power ratio exceeds a first threshold value associated with left carotid artery stenosis, and concludes that right carotid artery stenosis is present when the right high frequency power ratio exceeds a second threshold value associated with right carotid artery stenosis.

The data analysis system typically records values for the detected and characterized cardiovascular stenosis to a medical record for the individual, compares the recorded values to reference values for each of the recorded values, and sends notification messages to the individual and to medical professionals when the results of the comparisons exceed threshold levels for each of the reference values. In examples, the reference values might be previously stored baseline values for the individual, or previously stored baseline values for cohorts of the individual.

In another example, the data analysis system calculates a high frequency power ratio for the cardiac signals that relates a high frequency power calculated for a ventricular diastole of the cardiac signals during a cardiac cycle to a high frequency power calculated for the cardiac cycle. The data analysis system then compares the high frequency power ratio to a threshold value to detect whether aortic regurgitation is present.

In general, according to another aspect, the invention features a cardiovascular stenosis monitoring, diagnosis, analysis and reporting method. The method comprises receiving biosignals including infrasonic cardiac signals from one or more earbuds worn by an individual, at an interface, and detecting and characterizing cardiovascular stenosis of the individual based upon the received biosignals.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings:

FIG. 3A shows a portion of the cardiac signal from the left earbud, and FIG. 3B shows a portion of the cardiac signal from the right earbud;

FIG. 6A is an ECG plot obtained by an ECG system, FIG. 6B is a plot obtained by an aortic catheter system, and FIG. 6C is a plot obtained by the CV stenosis system;

FIG. 9A is an ECG plot; FIG. 9B is a blood pressure plot from an aortic catheter; FIG. 9C is a biosignal plot; FIG. 9D is a plot of cardiac signals/cardiac signal components of the biosignals in FIG. 9C that are less than 15 Hz; and FIG. 9E is a plot of signal components of the biosignals in FIG. 9C that are greater than 15 Hz.

DETAILED DESCRIPTION OF THE PREFERRED EMBODIMENTS

The invention now will be described more fully hereinafter with reference to the accompanying drawings, in which illustrative embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

As used herein, the term "and/or" includes any and all combinations of one or more of the associated listed items. Further, the singular forms and the articles "a", "an" and "the" are intended to include the plural forms as well, unless expressly stated otherwise. It will be further understood that the terms: includes, comprises, including and/or comprising, when used in this specification, specify the presence of stated features, integers, steps, operations, elements, and/or components, but do not preclude the presence or addition of one or more other features, integers, steps, operations, elements, components, and/or groups thereof. Further, it will be understood that when an element, including component or subsystem, is referred to and/or shown as being connected or coupled to another element, it can be directly connected or coupled to the other element or intervening elements may be present.

It will be understood that although terms such as "first" and "second" are used herein to describe various elements, these elements should not be limited by these terms. These terms are only used to distinguish one element from another element. Thus, an element discussed below could be termed a second element, and similarly, a second element may be termed a first element without departing from the teachings of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Figure 1:
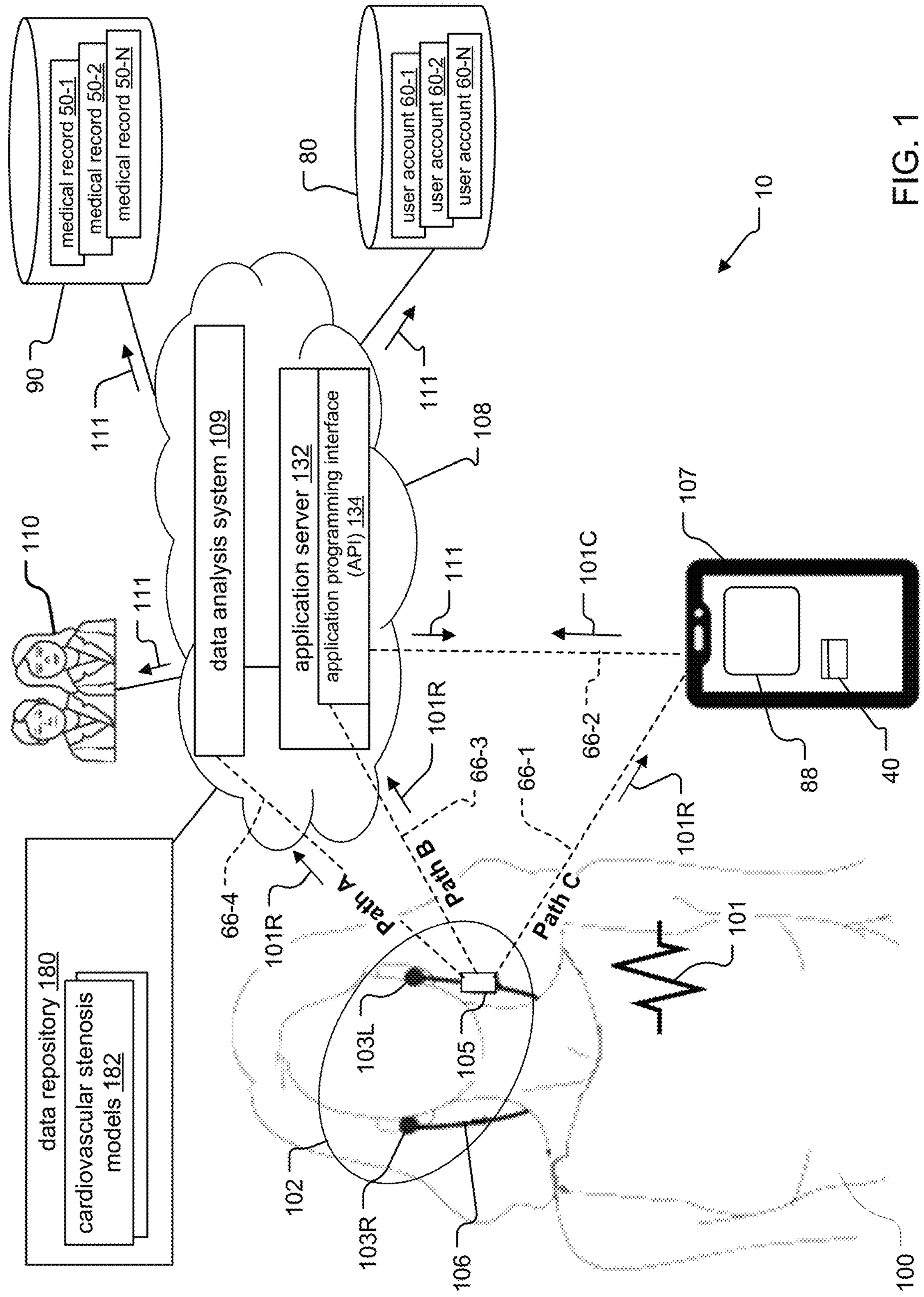
FIG. 1 is a schematic diagram of an exemplary cardiovascular stenosis monitoring, diagnosis, analysis and management system ("CV stenosis system") constructed in accordance with principles of the present invention, where the CV stenosis system includes an in-ear biosensor system that detects biosignals from an individual and a cloud-based data analysis system that analyzes the biosignals.

FIG. 1 is a schematic diagram of an exemplary cardiovascular stenosis monitoring, diagnosis, analysis and management system ("CV stenosis system") 10 constructed in accordance with principles of the present invention. The CV stenosis system 10 includes an in-ear biosensor system 102 worn by an individual 100, a user device 107 carried by the individual 100 and various components within and/or in communication with a network cloud 108.

The components within and/or in communication with the network cloud 108 include a data analysis system 109 and an application server 132, a medical record database 90, a user account database 80 and a data repository 180. The medical record database 90 includes medical records 50 of individuals 100, while the user account database 80 includes user accounts 60 of individuals 100 that are authorized users of the system 10. The data repository 180 includes cardiovascular stenosis models 182.

A computing device includes at least one or more central processing units (CPUs) and a memory. The CPUs have internal logic circuits that perform arithmetic operations and execute machine code instructions of applications ("application code") loaded into the memory. The instructions control and communicate with input and output devices (I/O) such as displays, printers and network interfaces.

The CPUs of the computing devices are typically configured as either microprocessors or microcontrollers. A microprocessor generally includes only the CPU in a physical fabricated package, or "chip." Computer designers must connect the CPUs to external memory and I/O to make the microprocessors operational. Microcontrollers, in contrast, typically integrate the memory and the I/O within the same chip that houses the CPU.

The CPUs of the microcontrollers and microprocessors of the computing devices execute application code that extends the capabilities of the computing devices. In the microcontrollers, the application code is typically pre-loaded into the memory before startup and cannot be changed or replaced during run-time. In contrast, the CPUs of the microprocessors are typically configured to work with an operating system that enables different applications to execute at different times during run-time.

The operating system has different functions. The operating system enables application code of different applications to be loaded and executed at run-time. Specifically, the operating system can load the application code of different applications within the memory for execution by the CPU, and schedule the execution of the application code by the CPU. In addition, the operating system provides a set of programming interfaces of the CPU to the applications, known as application programming interfaces (APIs). The APIs allow the applications to access features of the CPU while also protecting the CPU. For this reason, the operating system is said to execute "on top of" the CPU. Other examples of CPUs include Digital Signal Processors (DSPs), Application Specific Integrated Circuits (ASICs), and Field Programmable Gate Arrays (FPGAs).

The in-ear biosensor system 102 includes left and right earbuds 103L, 103R and a controller board 105. The earbuds 103 communicate with one another and with the controller board 105 via earbud connection 106. Here, the earbud connection 106 is a wired connection, but wireless connections are also supported. Here, the controller board 105 is an external component, but the controller board 105 can be also embedded in the earbuds 103L, 103R.

The user devices 107 include portable user devices and stationary user devices. In examples, the portable user devices include mobile phones, smart glasses, smart watches, and laptops, in examples. The stationary user devices include workstations and gaming systems, in examples. A mobile phone/smartphone user device 107 is shown.

Each user device 107 is a computing device that includes a display 88 and one or more applications. An interactive user application running on each user device 107, or user app 40, is shown. The user app 40 of each user device 107 executes upon a CPU of the user device 107, receives information sent by other components in the system 10 and presents a graphical user interface (GUI) on the display 88. The GUI allows the individual 100 to enter information at the user app 40 and can display various information upon the display 88.

The application server 132 is a computing device that connects client devices to components within or at the network cloud 108. The client devices include the in-ear biosensor system 102 and the user devices 107. The application server 132 includes secure website software (or a secure proprietary application) that executes on the application server 132. The application server 132 also includes an application programming interface ("API") 134.

Medical professionals 110 are also shown. The medical professionals 110 include doctors, nurses/nurse practitioners, physician's assistants, and medical technicians, in examples. The medical professionals 110 are trained in the use of the existing medical diagnosis equipment and the CV stenosis system 10. The medical professionals use computing devices such as laptops or smartphones to securely connect to the network cloud 108. In examples, the medical professionals 110 can connect to the network cloud 108 through telehealth services, or virtual clinics, with user 100 information provided by the CV stenosis system 10.

The medical professionals 110, the databases 80/90, the user devices 107 and the data repository 180 can connect to the network cloud 108 and/or components within the cloud 108 in various ways. These connections can be wired Internet-based or telephony connections, wireless cellular connections, and/or wireless Internet-based connections (e.g., Wi-Fi), in examples. In examples, the network cloud 108 can be a public network, such as the Internet, or a private network.

The in-ear biosensor system 102 and the user devices 107 communicate with each other and with the network cloud 108 via one or more wireless communications links 66. In more detail, the user device 107 connects to the in-ear biosensor system 102 via wireless link 66-1 and connects to the application server 132 via wireless link 66-2. The in-ear biosensor system 102 can also communicate with the application server 132 via wireless link 66-3 and might connect directly to the data analysis system 109 via wireless link 66-4. The wireless links 66 might be cellular-based or Internet-based (e.g., IEEE 802.11/Wi-Fi), or possibly even Bluetooth. In one example, the wireless links 66-3 and 66-4 are high-speed 5G cellular links. These links 66 are also encrypted to provide secure communications between the components that are at endpoints of the links 66.

In the illustrated example, the data analysis system 109 and the application server 132 are located in the network cloud 108. The network cloud 108 is remote to the individual 100. In this way, the application server 132 and the data analysis system 109 can service possibly thousands or more individuals 100 that are in different geographically distributed locations. Alternatively, the data analysis system 109 and/or the application server 132 might also be located on a local area network within a premises, such as a residence, commercial building or place of business of the individual 100. In one implementation, the capabilities provided by the application server 132 are incorporated into the data analysis system 109.

The API 134 enables exchange of information between the clients of the system 10 and the network cloud 108. The API also prevents the clients from accessing or modifying internal data, files and other resources of the components within the network cloud 108. For this purpose, the API 134 presents a set of public software interfaces which the clients can access. The public software interfaces, in turn, map to internal software and/or firmware functions and methods of the application server 132 that reference or otherwise access private data, files and other resources of the application server 132, the data analysis system 109, and/or other components of the network cloud 108.

In another implementation, the API 134 is included within the data analysis system 109. In this example, the clients of the system 10 are first authorized by the application server 132, and the application server forwards information sent by the authorized clients to the API 134 of the data analysis system 109.

Infrasound

Biosignals such as acoustic signals are generated internally in the body by breathing, heartbeat, coughing, muscle movement, swallowing, chewing, body motion, sneezing and blood flow, in examples. The acoustic signals can be also generated by external sources, such as air conditioning systems, vehicle interiors, various industrial processes, etc. The acoustic signals include audible and infrasonic signals.

The acoustic signals represent fluctuating pressure changes superimposed on the normal ambient pressure of the individual's body and can be defined by their spectral frequency components. Sounds with frequencies ranging from 20 Hz to 20 kHz represent those typically heard by humans and are designated as falling within the audible range. Sounds with frequencies below the audible range (i.e., from 0 Hz to 20 Hz) are termed infrasonic or infrasound. The level of a sound is normally defined in terms of the magnitude of the pressure changes it represents. These changes can be measured and do not depend on the frequency of the sound.

The left and right earbuds 103L,103R detect the biosignals 101 from the individual 100 via sensors included within one or more of the earbuds 103. These sensors include acoustic sensors, which can detect sounds in both the infrasonic and audible ranges, vibration sensors and pressure sensors, and possibly dedicated infrasonic sensors, in examples.

The biologically-originating sound detected inside the ear canal by the earbuds 103 is mostly in the infrasound range. In particular, the infrasound and vibration sensors can detect biosignals from the individual 100 that include information associated with operation of the individual's cardiovascular system and musculoskeletal system. The signal information associated with operation of the individual's cardiovascular and musculoskeletal systems are also known as cardiac signals and musculoskeletal signals, respectively.

The cardiac signals and the audible signals are separate components of the biosignals 101. The in-ear biosensor system 102 sends the biosignals 101 to the data analysis system 109 for analysis.

Typically, the biosignals are detected at each of the earbuds 103L,R at substantially the same times. This "stereo effect" can be utilized to identify and address artifacts, as well as improve a signal to noise ratio (SNR) of the biosignals 101 and thus provide high quality signals for subsequent characterization and analysis.

The CV stenosis system 10 generally operates as follows. An individual enters his/her credentials at the GUI of the user app 40, which the user device 107 sends over link 66-2 to the application server 132. The application server 132 receives the credentials and verifies that the credentials are associated with an authorized user of the CV stenosis system 10. For this purpose, the secure website software at the application server 132 compares the received credentials to those stored within the user accounts 60 of the user account database 80. Upon finding a match, the application server 132 establishes an authenticated, secure login session over wireless connection 66-2 between the user app 40 and the application server 132 for the individual 100 as an authorized user of the CV stenosis system 10.

The user app 40 might also determine whether the in-ear biosensor system 102 is paired to the proper authorized user. For this purpose, the user app 40 might access an identifier such as a serial number of the in-ear biosensor system 102 that the individual 100 previously entered into the user app 40. The user app 40 then queries the controller board 105 of the in-ear biosensor system 102 to obtain its identifier, and matches the obtained identifier to the locally stored identifier.

At the same time, the earbuds 103L,103R of the in-ear biosensor system 102 continuously detect and collect the biosignals 101 from the individual 100 and send the biosignals 101 to the controller board 105. Here, the biosignals are in "raw" format: they are uncompressed and may include some noise and/or motion artifacts. In another embodiment, the biosignals 101 might also be compressed, filtered, and pre-analyzed. The controller board 105 buffers the biosignals 101 for subsequent secure transmission to the data analysis system 109.

Once the application server 132 indicates to the user device 107 that the individual 100 is an authorized user, the user device 107 signals the controller board 105 to send the detected biosignals 101 to the data analysis system 109 by way of one or more communications paths. These paths are labeled Path A, B, and C in the figure. These paths respectively include zero, one, or more than one intermediary components or "hops" between the controller board 105 and the data analysis system 109. The decision of whether to send the biosignals 101 along the different paths depends on factors including the CPU speed of the components at the endpoints of the links 66, the buffer sizes of the wireless transceivers in the components that form each path, and characteristics of the wireless links 66 that form the communications paths. These characteristics include speed, level of encryption and available bandwidth, in examples. A description for each Path A, B and C follows hereinbelow.

Path C is typically the slowest communications path. This path includes wireless links 66-1 and 66-2, and includes the user device 107 and the application server 132 as intermediary components between the in-ear biosensor system 102 and the data analysis system 109. In more detail, the controller board 105 first sends raw versions of the detected biosignals over link 66-1 to the user device 107, indicated by reference 101R. The user app 40 then compresses the raw biosignals 101R into compressed versions of the biosignals 101C for transmission over link 66-2 to the application server 132.

In the illustrated example, the API 134 of the application server 132 receives the compressed biosignals 101C from the user device 107. The application server 132 then decompresses the compressed biosignals 101C and forwards the (uncompressed) biosignals 101 to the data analysis system 109. The API 134 can also act as an intermediary for any signals or messages sent between the data analysis system 109 and the user device 107 client.

Path B is generally faster than Path C. Path B includes wireless link 66-3 and only one intermediary component, the application server 132, between the controller board 105 and the data analysis system 109. Because link 66-3 is a fast or high throughput link (such as a 5G cellular link), the controller board 105 can send the raw biosignals 101R over link 66-3 to the application server 132 without having to compress the signals prior to transmission.

Also in regards to Path B, the API 134 can receive the biosignals 101 from the controller board 105. The application server 132 can perform various operations on the raw biosignals 101R before forwarding the signals to the data analysis system 109 for analysis. These operations include filtering and characterization, authentication, and/or buffering of the signals. As with Path C, the API 134 can also act as an intermediary for any signals or messages sent between the data analysis system 109 and the controller board 105. In this way, the in-ear biosensor system 102 operates as a client of the application server 132/data analysis system 109, via the API 134.

Path A is typically the fastest path because it utilizes direct link 66-4 to the data analysis system 109. As a result, the in-ear biosensor system 102 can send the raw biosignals 101R directly to the data analysis system 109. As noted herein above, the data analysis system 109 might also include an API 134 that operates as a communications intermediary between the controller board 105 and the data analysis system 109.

The data analysis system 109 then analyzes the biosignals 101 and can use information from the data repository 180 during the analysis. In one example, the data analysis system 109 can use the cardiovascular stenosis models 182 when detecting and characterizing a level of cardiovascular stenosis. The data analysis system 109 and/or the application server 132 can access and update the medical record 50 of the individual 100 during and in response to the analysis.

The data analysis system 109 can also send various notification messages 111 in response to the analysis of the biosignals 101. The notification messages 111 include information concerning the analysis and the results of the analysis. The messages 111 can be sent to the medical professionals 110, the databases 80/90, the user devices 107, and possibly even the controller board 105 of the in-ear biosensor system 102. The notification messages 111 can be in the form of an email, SMS/text message, phone call, database record in proprietary format or XML or CSV format, or possibly even audible speech, in examples.

The data analysis system 109 can also notify the individual 100 both during and after the analysis via the notification messages 111. In one example, the user app 40 receives the notification messages 111 and might present the notification messages 111 at the display 88, or forward the messages 111 over the wireless link 66-1 to the in-ear biosensor system 102. In another example, the messages 111 might be audible sound messages prepared by the data analysis system 109 or sent by the application server 132 or user device 107 to the connector board 105, for subsequent audio presentation at speakers included within the earbuds 103L,103R.

In this way, the CV stenosis system 10 can continuously monitor and analyze biosignals 101 including infrasound signals detected by and sent from in-ear biosensor systems 102 worn by different individuals 100, and identify and characterize aspects of the biosignals 101. The system 10 can also update medical records 50 for each of the individuals 100, report problems/notify medical professionals 110 of likely medical issues found during the analysis, and provide feedback to the individuals 100 during and upon completion of the analysis.

As a result, the CV stenosis system 10 includes an interface 134 configured to receive biosignals 101 including infrasonic cardiac signals from one or more earbuds 103 worn by an individual 100 and includes a data analysis system 109. The data analysis system detects and characterizes cardiovascular stenosis of the individual 100 based upon the received biosignals 101.

Figure 2:
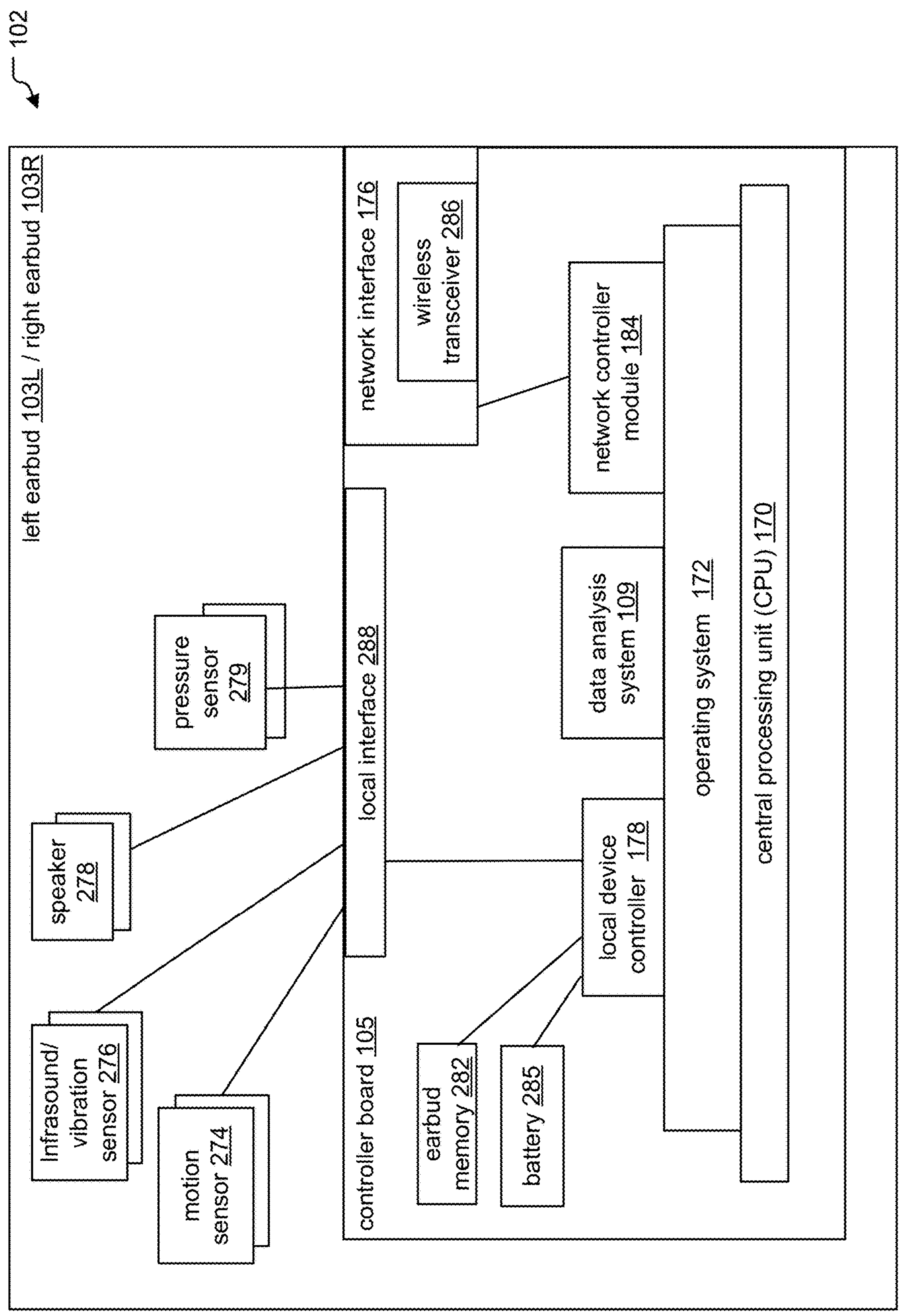
FIG. 2 is a schematic diagram showing detail for the in-ear biosensor system, according to an embodiment.

FIG. 2 shows detail for an embodiment of the in-ear biosensor system 102. In the illustrated example, both of the earbuds 103L,R are configured in substantially the same way, include substantially the same components and operate as microprocessors.

In the illustrated example, the earbuds 103 each include various sensors and a controller board 105. In more detail, the sensors in each earbud include one or more motion sensors 274, one or more acoustic sensors such as infrasound/vibration sensors 276, one or more speakers 278 and one or more pressure sensors 279. The motion sensors include accelerometers and gyroscopes, in examples. The infrasonic/vibration sensors 276 operate in the infrasonic range and might also operate in the audible range. In another example, two or more acoustic sensors in each earbud can detect sound in different frequency ranges (e.g., one for detecting infrasounds and the other for detecting audible sounds).

The pressure sensors 279 serve multiple purposes. In one example, the pressure sensors 279 can be used to characterize a level of seal/occlusion of each earbud 103 with respect to the individual's ear canals. In another example, the sensors 279 can be used to monitor changes in baseline pressure in the ear canal(s) due to, for example, physiological changes. These pressure sensors 279 are examples of auxiliary sensors that can detect pressure biosignals in the individual's ear to monitor occlusion level of one or both of the earbuds 103L,R and to monitor physiological changes of the individual 100.

The controller board 105 has a local interface 288 and includes earbud memory 282, a battery 285, a network interface 176, an operating system 172 and a CPU 170. The network interface 176 includes a wireless transceiver 286. The sensors 274, 276, 279 and the speakers 278 connect to the controller board 105 via the local interface 288. The controller board 105 provides power to each earbud 103 and enables communications between each earbud and external components via the network interface 176.

The controller board 105 also includes one or more modules, a local device controller 178 and a data analysis system/module 109. The local device controller 184 and the modules sit on top of the operating system 172 and execute on the CPU 170.

The sensors 274, 276, 279 detect various information including sounds and vibrations, motion and pressure originating from the individual 100 and send biosignals 101 representing the information to the controller board 105. In one example, the sounds and vibrations are in the infrasonic range and are represented as cardiac signals within the biosignals 101. These infrasounds and vibrations are typically associated with operation of the individual's heart and its various chambers and valves, and can also be associated with other cardiovascular components such as the lungs, arteries, veins, coronary and portal vessels. Additionally, the sounds from the individual 100 can be in the audible frequency range. These sounds can include those associated with breathing and snoring, in examples. The motion sensors 274 detect movement of the individual (e.g., moving, sneezing, eye and head movements, arm and leg movements), and represent the motion as motion artifacts within the biosignals 101. The pressure sensors 279 detect pressure within the inner ear canal and represent the pressure as pressure signals within the biosignals 101.

The controller board 105 also receives information from other components in the CV stenosis system 10 via the network interface 176. This information includes the notification messages 111 for presentation at the earbuds 103L, 103R, and commands sent from the user app 40. In another example, the information includes updates for application code running within the CPU 170.

Each earbud 103 generally operates as follows. The sensors 274, 276, 279 detect sounds and pressure from the individual 100 and send biosignals 101 representing this information and the pressure to the local interface 288. The local device controller 178 receives the biosignals 101 via the local interface 288 and forwards the signals via the operating system 172 and the CPU 170 for processing by various modules that sit on top of the operating system 172.

In another implementation, only one of the earbuds such as the left earbud 103L is configured as shown, while the other earbud (the right earbud 103R) does not include a controller board 105. Here, the right earbud 103R includes only the sensors 274, 276, 279 and the speaker 278 and has a wired earbud connection 106 to the left earbud 103L. The right earbud 103R receives its source of power over the wired earbud connection 106 from the left earbud 103L, and sends its detected signals over the wired earbud connection 106 to the left earbud 103L for processing and analysis.

In still another implementation, neither of the earbuds 103L,R include a controller board 105. Instead, both of the earbuds 103L,R include only the sensors 274, 276, 279 and the speaker 278. The earbuds 103L,R connect to a common controller board 105 located along a wired earbud connection 106 between the earbuds 103, and each receive a source of power from the controller board 105. The sensors 274, 276, 279 of each earbud 103L,R send their detected signals over the wired earbud connection 106 to the controller board 105 and its data analysis system 109 for processing and analysis.

In yet another implementation, neither of the earbuds 103L,R shown in FIG. 2 include a data analysis module/system 109. The sensors 274, 276, 279 of each earbud 103L,R send their detected signals via the network interface 176 to an external data analysis system 109 for processing and analysis.

Figures 3A, 3B:
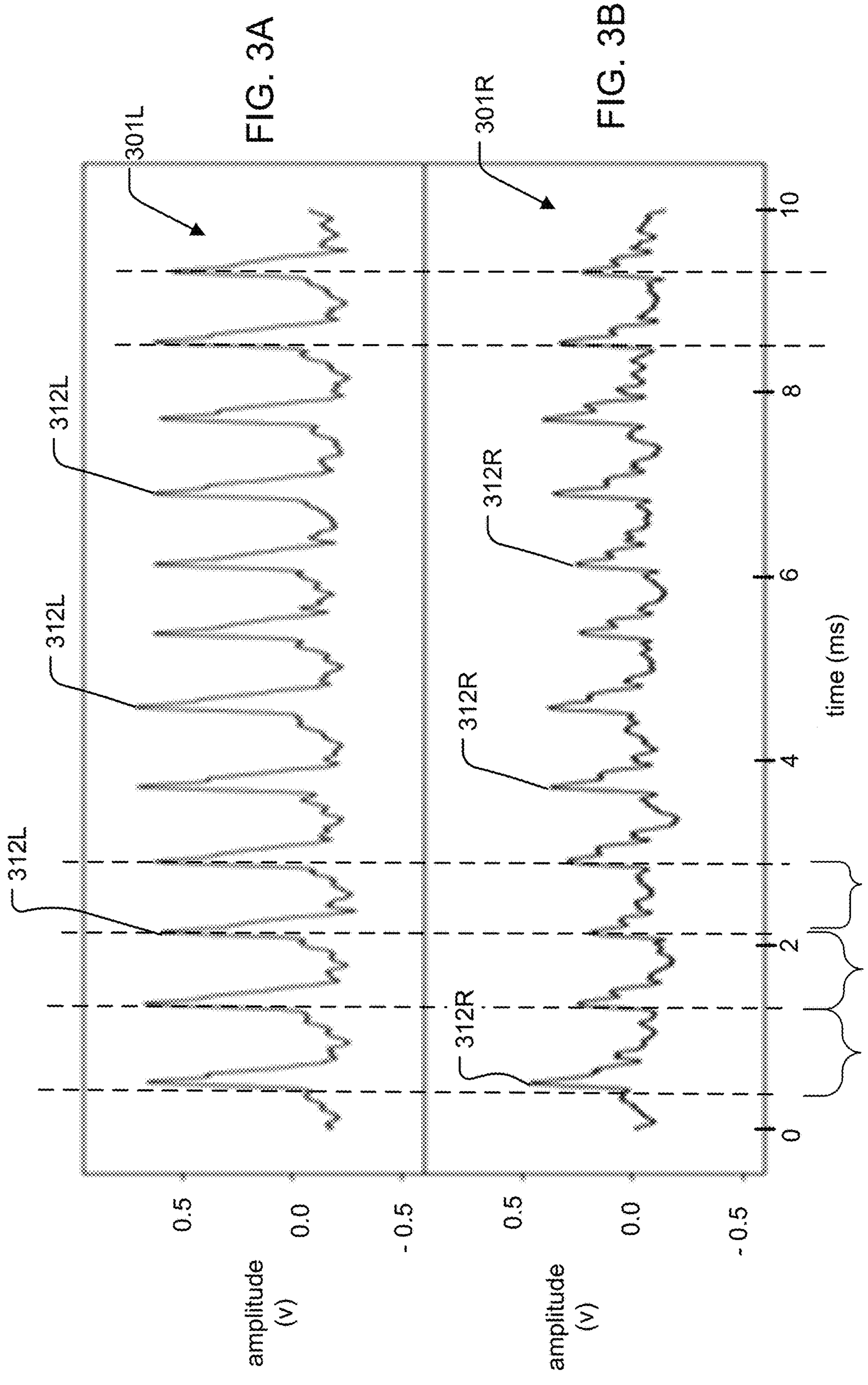
FIGS. 3A and 3B are plots of an infrasonic cardiac signal component of biosignals for a healthy individual, where the biosignals are detected by and sent by the in-ear biosensor system, where

FIGS. 3A and 3B are plots of cardiac signals 301 for a healthy individual. The cardiac signals 301 are the infrasonic components of the biosignals 101 obtained by the in-ear biosensor system 102 for the individual 100. FIG. 3A shows a portion of the cardiac signals 301 from the left earbud (left cardiac signals 301L), and FIG. 3B shows a portion of the cardiac signals from the right earbud (right cardiac signals 301R).

More detail for the plots of the cardiac signals 301 in FIGS. 3A and 3B is as follows. Systolic peaks 312 within the cardiac signals and cardiac cycles 310 are shown. The cardiac cycle 310 is the time between successive systolic peaks 312. Three successive cardiac cycles 310-1 through 310-3 are shown. Each cardiac cycle 310 of healthy individuals 310 is about 0.8 seconds long, as shown. Left and right systolic peaks 312L, 312R are indicated in the left cardiac signals 301L and right cardiac signals 310R, respectively.

Figure 4:
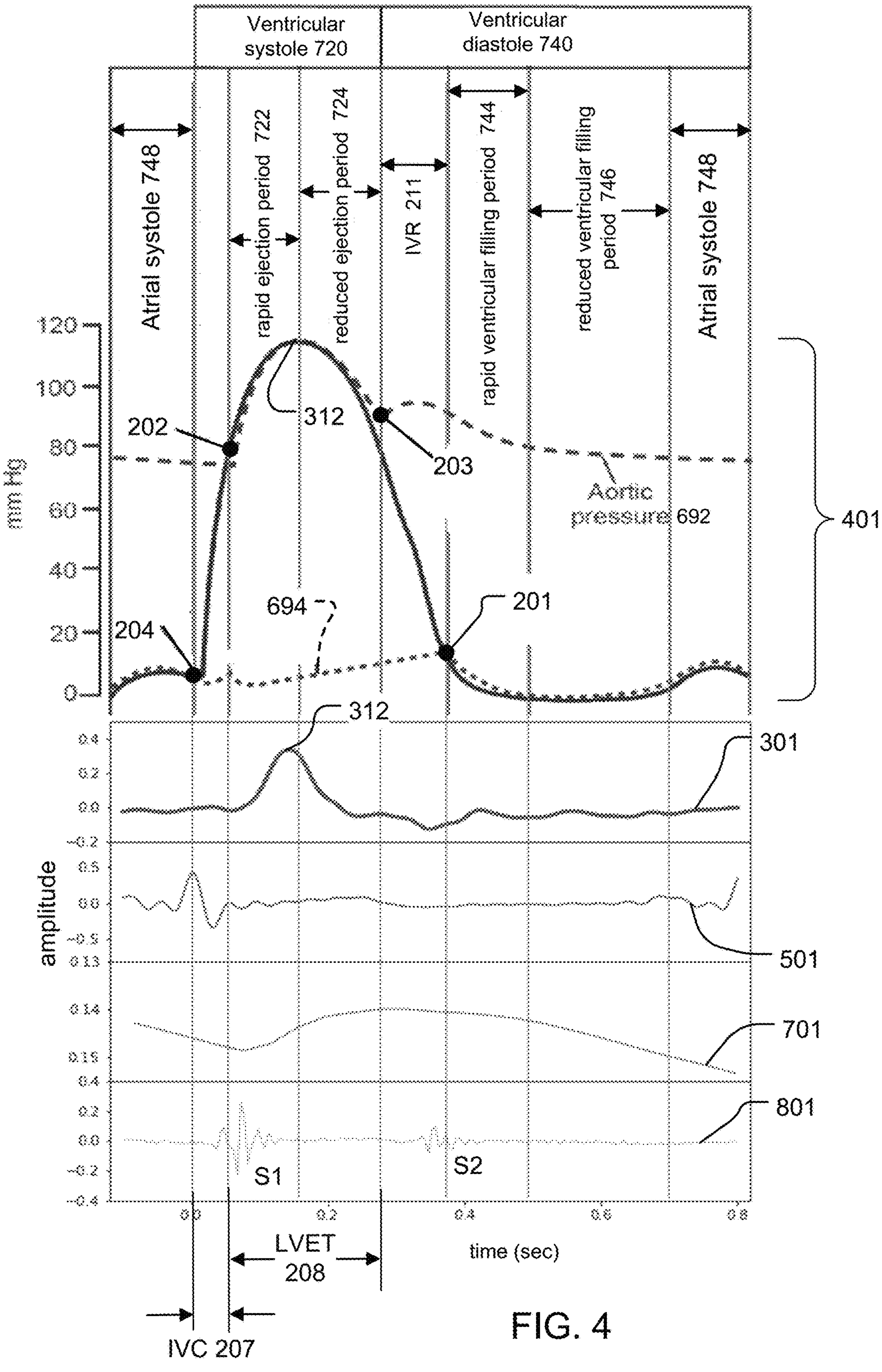
FIG. 4 is an augmented Wiggers diagram that illustrates operation of the left ventricle for an individual over a single cardiac cycle, where the diagram includes signal plots obtained by various existing stenosis diagnostics systems and s a plot of the cardiac signal obtained by the proposed CV stenosis system over the same time frame.

FIG. 4 is an augmented Wiggers diagram that illustrates operation of the left ventricle for an individual 100. The Wiggers diagram is produced by plotting signals associated with operation of the heart of the individual 100 over a single cardiac cycle 310, where the signals are obtained using different existing medical diagnostics equipment and using the CV stenosis system 10.

The plots are produced over the same time frame and initiated at the same time/synchronized. In this way, similarities and differences between the plots (and the capabilities of the different existing medical diagnostics equipment and the CV stenosis system 10) can be compared and contrasted.

From the top down, the diagram shows: a blood pressure (BP) signal 401 obtained by a catheter system; a cardiac signal 301 obtained by the CV stenosis system 10; an EKG/ECG signal 501 from an EKG/ECG system, a photoplethysmogram signal 701 obtained by a PPG system; and a phonocardiograph signal 801 from a PCG system. The pressure shown in this diagram is the aortic pressure 692. Each of the signals represent activity of the left ventricle of the heart of the individual 100 over a single cardiac cycle 310.

Various aspects of the signals 301, 401, 501, 701, and 801 are shown in the diagram. These aspects are either identified directly from the signals, or calculated/measured from the signals. These aspects include an atrial systole period 748, an isovolumetric contraction period (IVC) 207, a rapid ejection period (REP) 722, a reduced ejection period 724, an isovolumetric relaxation period (IVR) 211, a rapid ventricular filling period 744 and a reduced ventricular filling period 746. Heart sounds S1 and S2 in the phonocardiograph signal 801 are also displayed.

The aspects can also include cardiovascular parameters derived from the biosignals 101 including a peak aortic jet velocity, a mean transvalvular pressure gradient, and an aortic valve area. The CV stenosis system 10 can derive these cardiovascular parameters by comparing the biosignals 101 to predictions of the biosignals from numerical simulations of the cardiovascular system and the propagation of the biosignals 101. These cardiovascular parameters are examples of measurements used by the medical professionals 110 for clinical diagnosis and evaluation of aortic stenosis.

A ventricular systole 720 and a ventricular diastole 740 are also shown. The ventricular systole 720 is a cardiac phase that occurs over the combined time of the IVC 207, the rapid ejection period 722 and the reduced ejection period 724. The ventricular diastole 740 is a cardiac phase that occurs over the combined time of the IVR 211, the rapid ventricular filling period 744 and the reduced ventricular filling period 746.

Aortic stenosis is the most common type of cardiac stenosis and is usually caused by underlying problems with the aortic valve. Aortic stenosis is typically characterized by progressive narrowing of the aortic valve, which can result in decreased cardiac output, concomitant left ventricular pressure overload, and left ventricular hypertrophy. These physiologic changes commonly lead to symptoms of heart failure, syncope, and angina.

With reference to the plots and the aspects within the plots, an initial indication of aortic stenosis can be identified, in one example, as a delay in heart sound S2 that is reduced in intensity. Because PCG systems detect the amplitude and intensity of sound, the sound can be correlated to the severity of aortic stenosis).

Other aspects of the signals 301, 401, 501, 701, and 801 shown in the plots include a mitral valve opening time (MVO) 201, an aortic valve opening time (AVO) 202, an aortic valve closing time (AVC) 203 and a mitral valve closing time (MVC) 204.

Yet another aspect of the signals 301, 401, 501, 701, and 801 (or derived from these signals) is the left ventricle ejection time (LVET) 208. The LVET 208 is the time interval between the AVC 203 and the AVO 202.

Figure 5A:
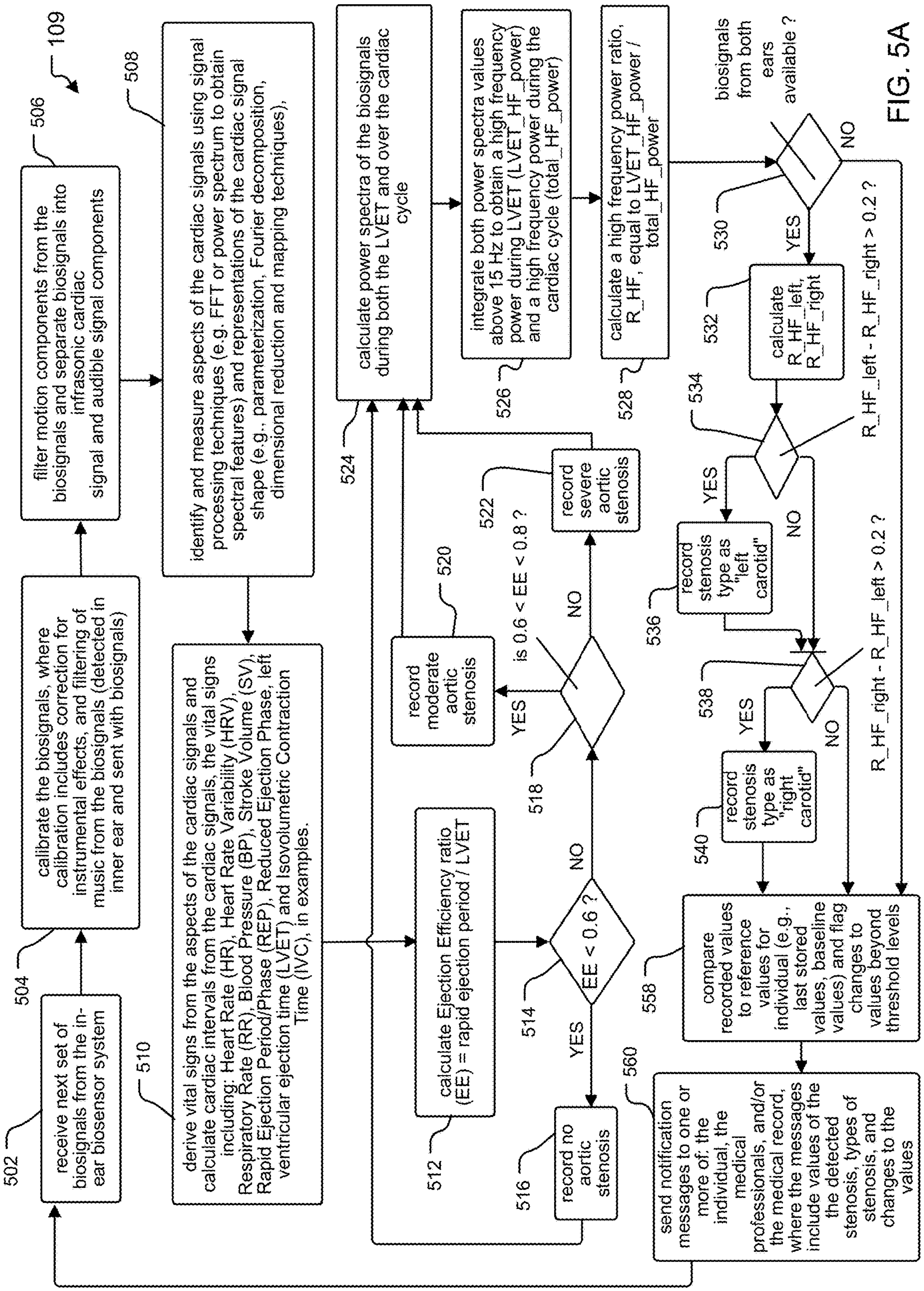
FIG. 5A is flow chart that illustrates a method of operation of the CV stenosis system, for detecting and diagnosing carotid artery stenosis and aortic stenosis.

FIG. 5A is a flow chart that illustrates a method of operation of the data analysis system 109. In the illustrated example, the method describes how the CV stenosis system 10 can calculate a level of aortic stenosis or carotid artery stenosis of an individual 100.

In the steps below, "the method" is a shorthand for operations performed by the data analysis system 109. The method starts at step 502.

In step 502, the data analysis system 109 receives the next set of biosignals from the in-ear biosensor system 102. In step 504, the data analysis system 109 calibrates the biosignals 101, where calibration includes correction for instrumental effects, and filtering of music from the biosignals. The earbuds 103 detect the music and the biosignals 101 in the inner ear and send the music along with the biosignals 101 to the controller board 105, which in turn forwards this information to the application server 132 and/or the data analysis system 109.

According to step 506, the method filters motion components from the biosignals and separates the biosignals 101 into infrasonic cardiac signal 301 and audible signal components.

In step 508, the method identifies and measures aspects of the cardiac signals 301 using signal processing techniques and representations of the cardiac signal shape. The cardiac signal shape representations can include the cardiac signal itself, Fourier components of the cardiac signal and singular value decomposition of the cardiac signal, in examples. The signal processing techniques can include calculating a Fast Fourier Transform (FFT) of the cardiac signals or obtaining a power spectra of the cardiac signals 301 to obtain spectral features. The aspects include features of the cardiac signals 301 and events that the data analysis system 109 obtains from the cardiac signals 301. These features and events include the AVO 202 and the AVC 203, the MVO 201 and the MVC 204, and the systolic peaks 312 of the cardiac signals 301.

Additionally or alternatively, the data analysis system 109 might identify and measure aspects of the cardiac signals 301 using machine learning algorithms and/or deep learning techniques. Examples of machine learning algorithms to identify/extract and measure these aspects include support vector classification/support vector machines, k-th nearest-neighbor algorithms, neural networks, linear discriminant analysis and decision trees.

According to step 510, the method derives vital signs from the aspects of the cardiac signals determined in step 508, and calculates cardiac intervals 310 from the cardiac signals 301. In examples, the vital signs include: Heart Rate (HR), Heart Rate Variability (HRV), Respiratory Rate (RR), Blood Pressure (BP), Stroke Volume (SV), the rapid ejection period 722 and the reduced ejection period 724. Other vital signs include the IVC 207 and the LVET 208, More detail for some of the vital signs and how they are calculated is as follows. The rapid ejection period 722 is calculated as the time between each systolic peak 312 and the AVO 202. The reduced ejection phase is the time of the systolic peak subtracted from the time of the AVC 203. The LVET 208 is the time between the AVO 202 and the AVC 203. The IVC 207 is the time interval between the MVC 204 and the AVO 202. During the IVC period 207, all valves of the heart are closed and the heart is contracting, yet there is no change in the blood volume of the ventricles.

Steps 512 through 522 describe how the data analysis system 109 can detect aortic cardiovascular stenosis and characterize the stenosis based upon the biosignals 101. For this purpose, the data analysis system 109 derives the LVET vital sign and the rapid ejection period (REP) vital sign from the biosignals 101, divides the REP by the LVET to obtain an Ejection Efficiency Ratio, and compares the Ejection Efficiency Ratio to threshold values to detect aortic cardiovascular stenosis and characterize its severity.

According to step 512, the method calculates an Ejection Efficiency ratio (EE), where EE=the rapid ejection period 722 divided by the LVET 208. Then, the method makes conclusions about the presence and level of stenosis based on the relative value of the EE. For this purpose, the method next transitions to step 514.

In step 514, the method determines whether the EE is less than a threshold value associated with aortic stenosis. Typically, this threshold is 60% (e.g., $EE<0.6$) and was obtained by comparing and averaging EE values of multiple individuals with known aortic stenosis. These individuals were previously diagnosed with aortic stenosis using one or more of the existing medical diagnostics systems such as the ECG system.

It can be appreciated that other threshold values or ranges of threshold values might also be used. These different threshold values can be associated with individuals of a specific age range, sex, nationality or ethnic group, in examples.

If the EE is less than the threshold value in step 514, the method concludes that no aortic stenosis is present in step 516 and records the event as "no aortic stenosis". The method then transitions back to step 524. If the EE is greater than or equal to the threshold value, however, the method concludes that the individual likely has aortic stenosis and transitions to step 518 to determine its level or severity.

It can also be appreciated that the CV stenosis system 10 can monitor individuals over time. For this purpose, the system 10 can detect changes to the EE ratio over time, and notify the individuals or medical professionals when the changes exceed one or more reference values or increase/decrease a predetermined percentage amount. For this purpose, in examples, the data analysis system 109 can compare the currently calculated EE ratio to reference values for the individual 100 or for groups of individuals/a cohort of the individual 100. In examples, the reference value might be a recently calculated and stored EE ratio for the individual 100 in the medical record 60 of the individual, or a baseline or average value of the EE for the individual in the medical record 60.

When the reference value is exceeded, the data analysis system can notify or alert the individual 100 by sending messages to the user device 107, audible messages via the earbuds 103, and notify the medical professionals 110. The data analysis system 109 can also send this information in notification messages to update the medical record 60. In still another example, when the EE for an individual 100 increases more than a predetermined percentage (e.g., five percent) as compared to a stored baseline EE value for the individual, the data analysis system can similarly notify or alert the individual, the medical professionals 110 and update the medical record 60.

In step 518, the method determines whether the EE is within a threshold range associated with moderate stenosis. Typically, this range is greater than 60% but less than 80% (i.e., $0.6<EE<0.8$). However, other ranges are also possible. If this condition is met, the method concludes that moderate stenosis exists and transitions to step 520 to record a "moderate aortic stenosis" event. Otherwise, because EE is equal to 0.8 or greater, the method concludes that severe stenosis exists and transitions to step 522 to record a "severe aortic stenosis" event. Upon conclusion of both steps 520 and 522, the method transitions to step 524.

According to steps 524 through 540, the method additionally or alternatively can detect carotid artery stenosis and characterize the stenosis as being associated with the left or right carotid artery based upon the biosignals 101. For this purpose, the method compares the left and right biosignals 103L, 103R. In more detail, in step 524, the method first calculates power spectra of the biosignals 101 during the LVET 208 of a cardiac cycle 310, and power spectra of the biosignals 101 over a full cardiac cycle 310 (for the cardiac cycle including the LVET 208). In step 526, the method then integrates both power spectra values above 15 Hz to obtain a high frequency power during LVET 208, or LVET_HF_power, and a high frequency power during the full cardiac cycle 310, or total_HF_power. Then, in step 528, the method calculates a high frequency power ratio, R_HF, expressed as the LVET_HF_power divided by the total_HF_power:

$$R\_HF = LVET\_HF\_power/total\_HF\_power$$

In step 530, the method determines whether biosignals 101 from both of the ears of the individual 100/from both earbuds 103L, 103R are available. When biosignals 101 from both ears are available, the method transitions to step 532; otherwise, the method transitions to step 558.

According to step 532, the method calculates a separate high frequency power ratio for the left and right biosignals 101L, 101R, also known as R_HF_left and R_HF_right, respectively, using the same techniques described in steps 524 through 528 hereinabove.

Then, in step 534, the method subtracts the value of the R_HF_right from the R_HF_left, and compares the difference to a threshold value. Typically, this threshold value is 0.2, but other values are possible. Specifically, when the difference is greater than the threshold value, the method concludes that left carotid artery stenosis is present, and transitions to step 536 to record the event as left carotid artery stenosis. The method then transitions to step 538. When the difference is equal to or less than the threshold value, the method transitions to step 538.

In step 538, the method subtracts the value of the R_HF_left from the R_HF_right, and compares the difference to a threshold value. Typically, this threshold value is 0.2, but other values are possible. Specifically, when the difference is greater than the threshold value, the method concludes that right carotid artery stenosis is present, and transitions to step 540 to record the event as right carotid artery stenosis. The method then transitions to step 558. When the difference is equal to or less than the threshold value, the method transitions to step 558.

As a result, the data analysis system 109 calculates the left high frequency power ratio R_HF_left for the left cardiac signal 301L from the left earbud 103L and calculates the right high frequency power ratio R_HF_left for the right cardiac signal 301R from the right earbud 103R. The left high frequency power ratio relates a high frequency power calculated for the LVET 208 of the left cardiac signal 301L during a cardiac cycle 310, to a high frequency power calculated for the left cardiac signal 301L over the cardiac cycle 310. In a similar vein, the right high frequency power ratio relates a high frequency power calculated for the LVET 208 of the right cardiac signal 301R during the cardiac cycle 310 to a high frequency power calculated for the right cardiac signal 301R over the cardiac cycle 310.

The data analysis system 109 then subtracts the right high frequency power ratio from the left high frequency power ratio and compares the difference to a threshold value to detect carotid artery cardiovascular stenosis and characterize it as left carotid artery cardiovascular stenosis. The data analysis system 109 also subtracts the left high frequency power ratio from the right high frequency power ratio to obtain a second difference, and compares the second difference to the threshold value to detect carotid artery cardiovascular stenosis and characterize it as right carotid artery cardiovascular stenosis.

In another embodiment, the method detects left carotid artery stenosis and right carotid artery stenosis in a mutually exclusive fashion. In more detail, the method compares R_HF_left to a threshold value associated with known left carotid artery stenosis. If the value of R_HF_left exceeds the threshold value, the method concludes that left carotid artery stenosis is present. In a similar vein, the method compares R_HF_right to a threshold value associated with known right carotid artery stenosis. If the value of R_HF_right exceeds the threshold value, the method concludes that right carotid artery stenosis is present.

At step 558, the method compares the recorded values for the stenosis to reference values for the individual (e.g., last stored values, baseline values) and flags changes to values beyond threshold levels. The method might also compare the recorded values for the stenosis to reference values for cohorts of the individual based on age range, sex, or ethic group, in examples. Because the system 10 maintains threshold values for each of the reference values (typically in the medical record 60 of the individual 100), the data analysis system 109 can alert the individual 100 or the medical professionals 110 when any of the recorded values obtained during the steps of the method have exceeded their threshold values.

As a result, the data analysis system 109 records values for the detected and characterized cardiovascular stenosis to the medical record 60 for the individual 100, compares the recorded values to reference values for each of the recorded values, and sends notification messages to the individual 100 and to the medical professionals 110 when the results of the comparisons exceed threshold levels for each of the reference values.

Then, in step 560, the method sends notification messages to one or more of the individual 100, the medical professionals 110 and/or the medical record 60 of the individual. The messages include values of the detected stenosis, type of stenosis (e.g. aortic, left carotid, right carotid) and the changes to the values beyond the threshold levels in step 558. For this purpose, the threshold values can be a fixed value or a percentage change, in examples.

The CV stenosis system 10 can also detect occurrences of aortic regurgitation using an analysis that is somewhat similar to that used in steps 526 and 528. In more detail, the data analysis system 109 calculates the power spectra of the biosignals 101 during the ventricular diastole 740 of a cardiac cycle 310, and power spectra of the biosignals 101 over a full cardiac cycle 310 (for the cardiac cycle including the ventricular diastole 740). The method then integrates both power spectra values above 15 Hz to obtain a high frequency power during ventricular diastole 740, or VD_HF_power, and a high frequency power during the full cardiac cycle 310, or total_HF_power. The method then calculates a high frequency power ratio, VD_HF, expressed as the VD_HF_power divided by the total_HF_power:

$$VD\_HF = VD\_HF\_power/total\_HF\_power$$

The method then determines whether aortic regurgitation has occurred by comparing VD_HF to a threshold value. In one example, the threshold value is 0.6. If the value of VD_HF exceeds the threshold value, the method concludes that aortic regurgitation is present.

As a result, the data analysis system 109 calculates a high frequency power ratio for the cardiac signals 301 that relates a high frequency power calculated for a ventricular diastole 740 of the cardiac signals during a cardiac cycle 310 to a high frequency power calculated for the cardiac cycle 310. The data analysis system 109 then compares the high frequency power ratio to a threshold value to detect whether aortic regurgitation is present.

Figure 5B:
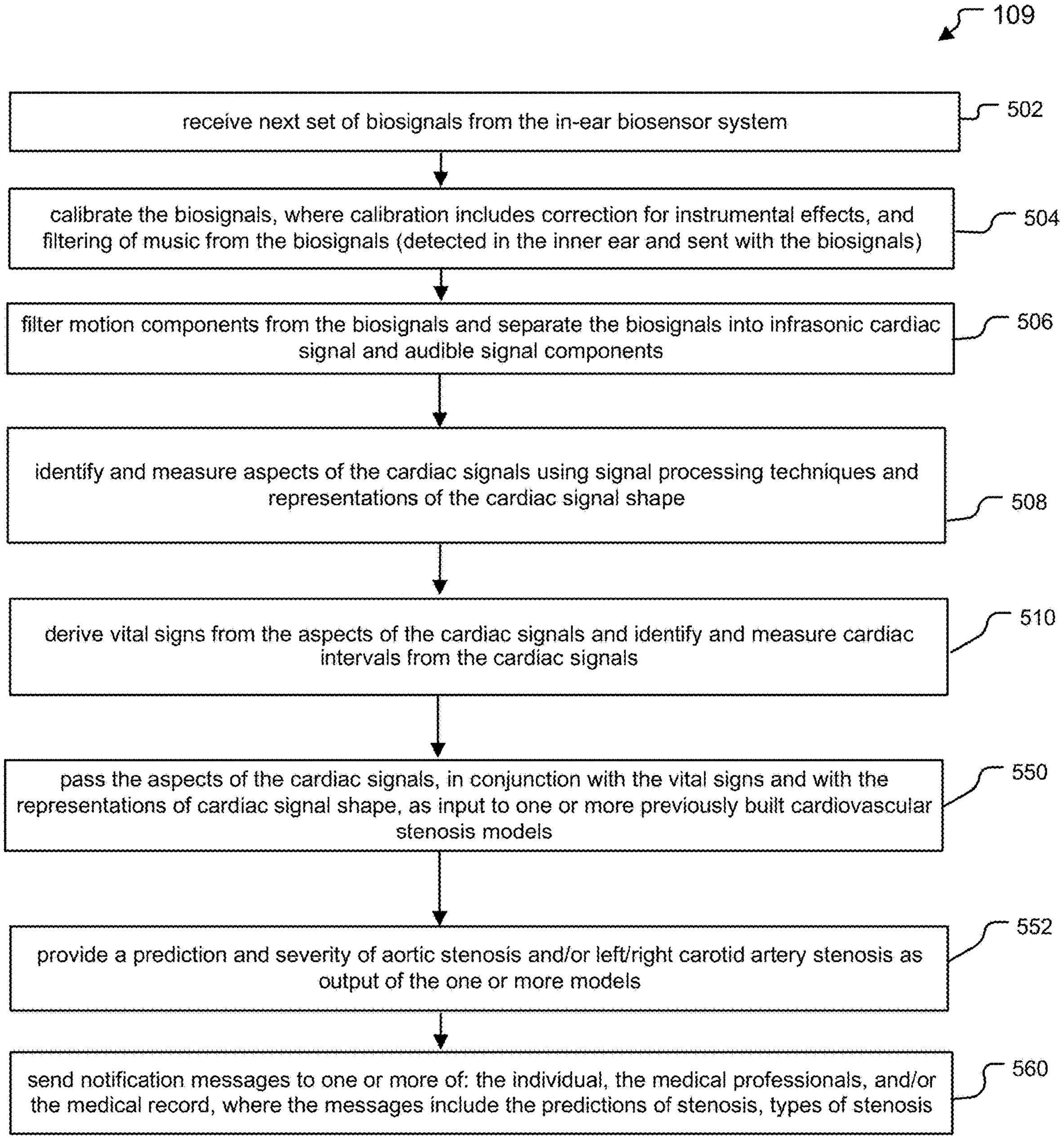
FIG. 5B is flow chart that illustrates another method of operation of the CV stenosis system, for detecting and diagnosing carotid artery stenosis and aortic stenosis.

FIG. 5B is a flow chart that illustrates another method of operation of the CV stenosis system 10. Here, the method uses machine learning to calculate or predict a level of stenosis and possibly the type of the stenosis (aortic stenosis or left/right carotid artery stenosis) of an individual 100.

Method steps 502-510 and 560 are substantially the same as in the method of FIG. 5A. Upon completion of step 510, the method transitions to step 550. In step 550, the method accesses the aspects of the cardiac signals 310, the representations of the cardiac signal shape, and the vital signs previously calculated or otherwise obtained in step 510. The method then passes the aspects of the cardiac signals 310 in conjunction with the vital signs and the representations of cardiac signal shape as input to one or more previously built cardiovascular stenosis models 182. According to step 552, the method then provides a prediction and severity/level of aortic stenosis and/or left/right carotid artery stenosis as output of the one or more models 182.

As a result, the data analysis system 1019 passes the aspects of the cardiac signals 301, in conjunction with the vital signs and with the representations of cardiac shape, as input to the one or more previously built cardiovascular stenosis models 182 to provide a prediction and severity of aortic stenosis and a prediction of left or right carotid artery stenosis as output of the one or more models 182.

The method then transitions to step 560 to send the results of the analysis in notification messages to the various destinations and recipients previously described herein above.

Figures 6A, 6B, 6C:
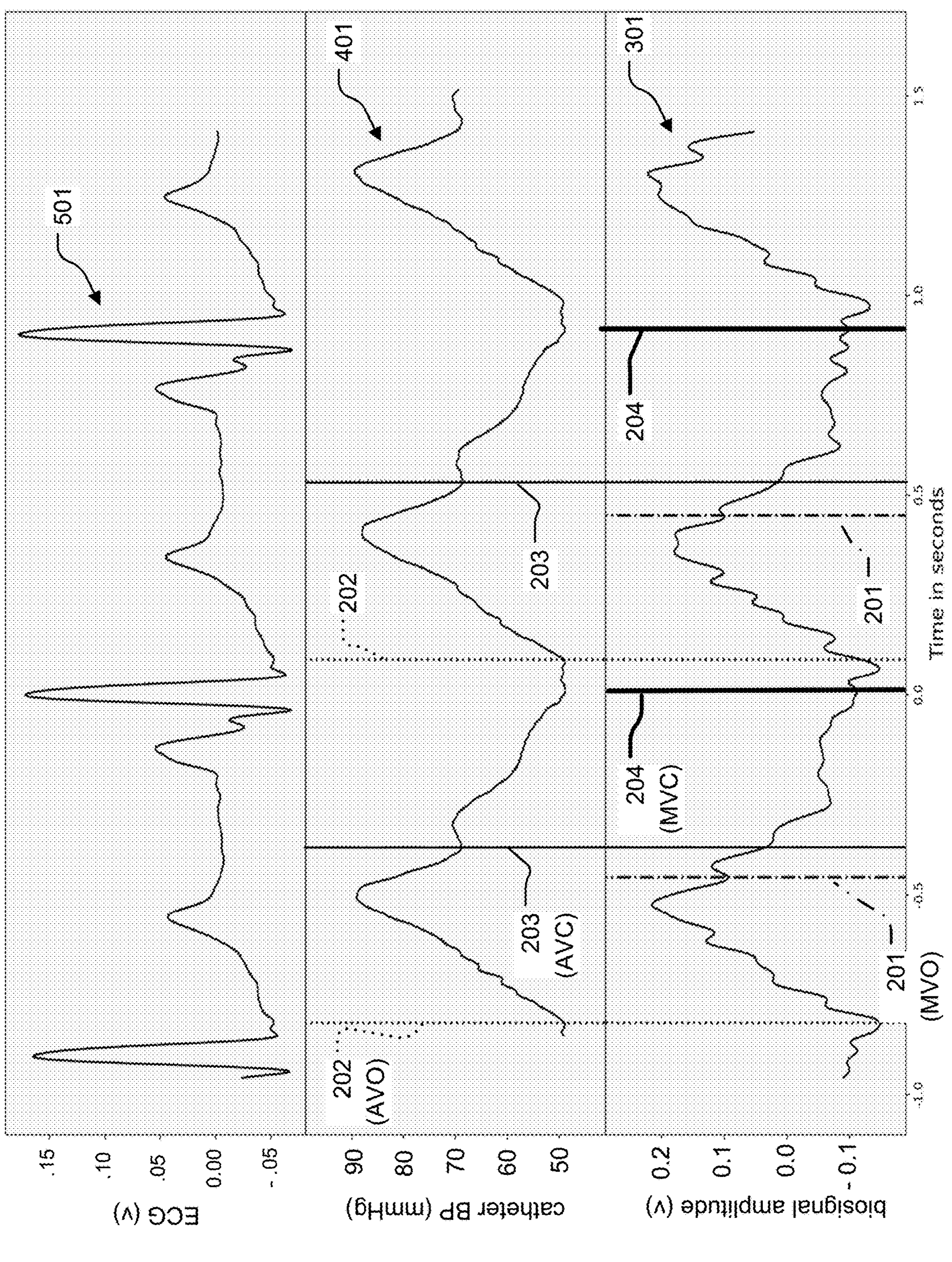
FIG. 6A-6C are signal plots of cardiac activity over the same time frame for an individual diagnosed with aortic valve stenosis, where

FIG. 6A through 6C show signal plots of an individual 100 with a damaged aortic valve. The damage is due to stenosis of the valve. FIG. 6A shows an ECG signal 501 obtained by an ECG system, FIG. 6B shows a BP signal 401 obtained by an aortic catheter system, and FIG. 6C shows a cardiac signal 301 obtained by the CV stenosis system 10. The plots were obtained and are presented over the same time frame for comparison.

Various aspects of the signals 301, 401, and 501 are also shown relative to the plots for comparison. These aspects include the cardiac cycle 310, the MVO 201, the AVO 202, the AVC 203, the MVC 204 and the systolic peaks 312 of the cardiac signals 301, in examples.

Figures 7A, 7B, 7C:
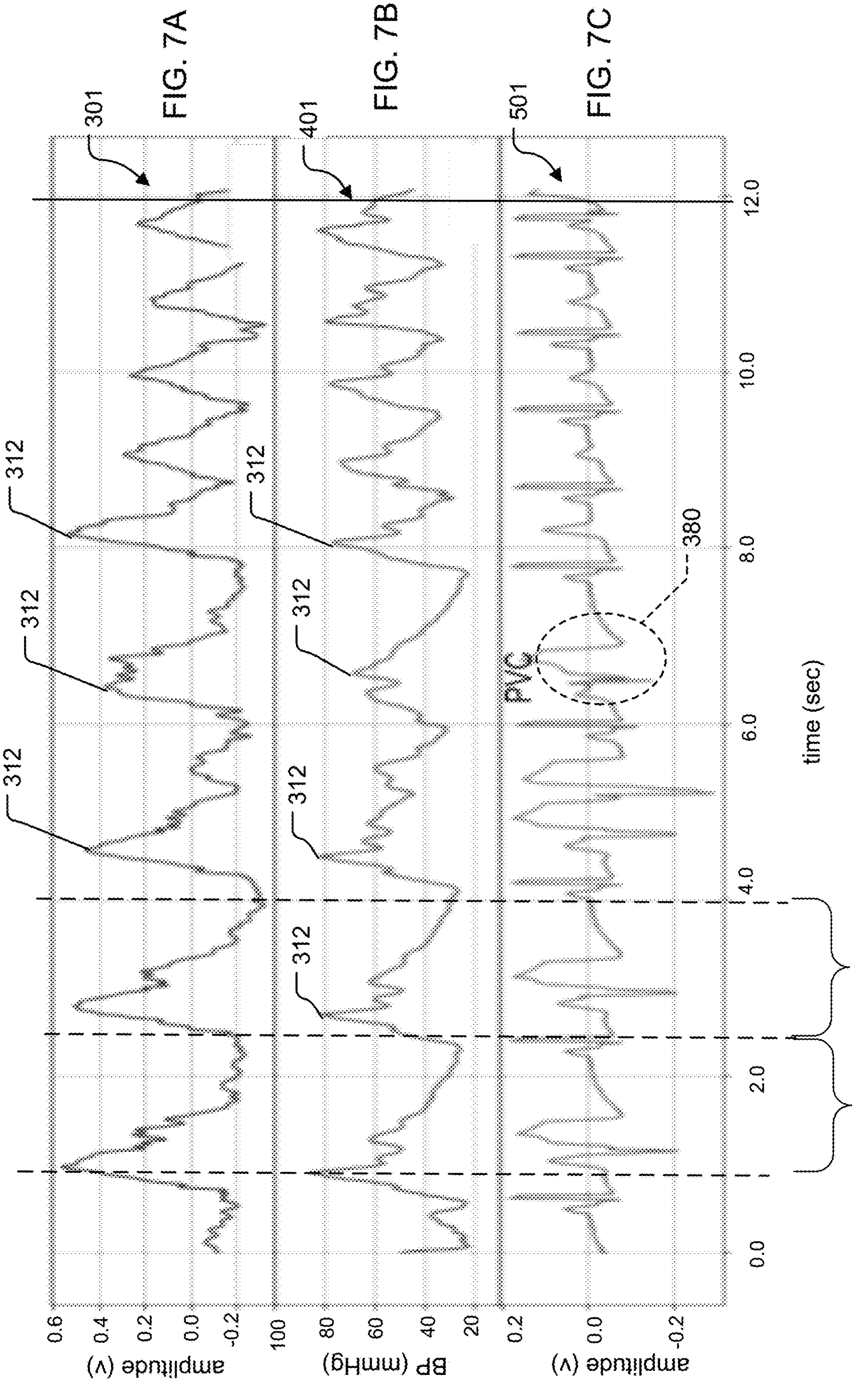
FIG. 7A-7C are plots of signals for the same individual as in FIG. 6A-6C, where the signal plots were respectively obtained by the proposed CV stenosis system, the aortic catheter system, and the ECG system for comparison, and where the plots were obtained just prior to the individual undergoing successful transcatheter aortic valve replacement (TAVR) surgery.

FIG. 7A-7C are signal plots for the same individual 100 with aortic stenosis as in FIG. 6A-6C. FIG. 7A shows a cardiac signal 301 obtained by the CV stenosis system 10, a BP signal 401 from an aortic catheter system, and an ECG signal 501 from an ECG system for comparison.

Here, the plots were obtained just prior to the individual undergoing successful transcatheter aortic valve replacement (TAVR) surgery. This surgery is a minimally invasive heart procedure to replace a damaged or narrowed aortic valve. A premature ventricular contraction (PVC) 380 is also indicated in the ECG signal 501. The CV stenosis system 10 can be used as a monitoring tool during a cardiac procedure, such as the TAVR surgery. The biosignal recording or measurements performed on the biosignal (e.g., stroke volume, blood pressure) can be displayed live during the TAVR procedure.

Figures 8A, 8B, 8C:
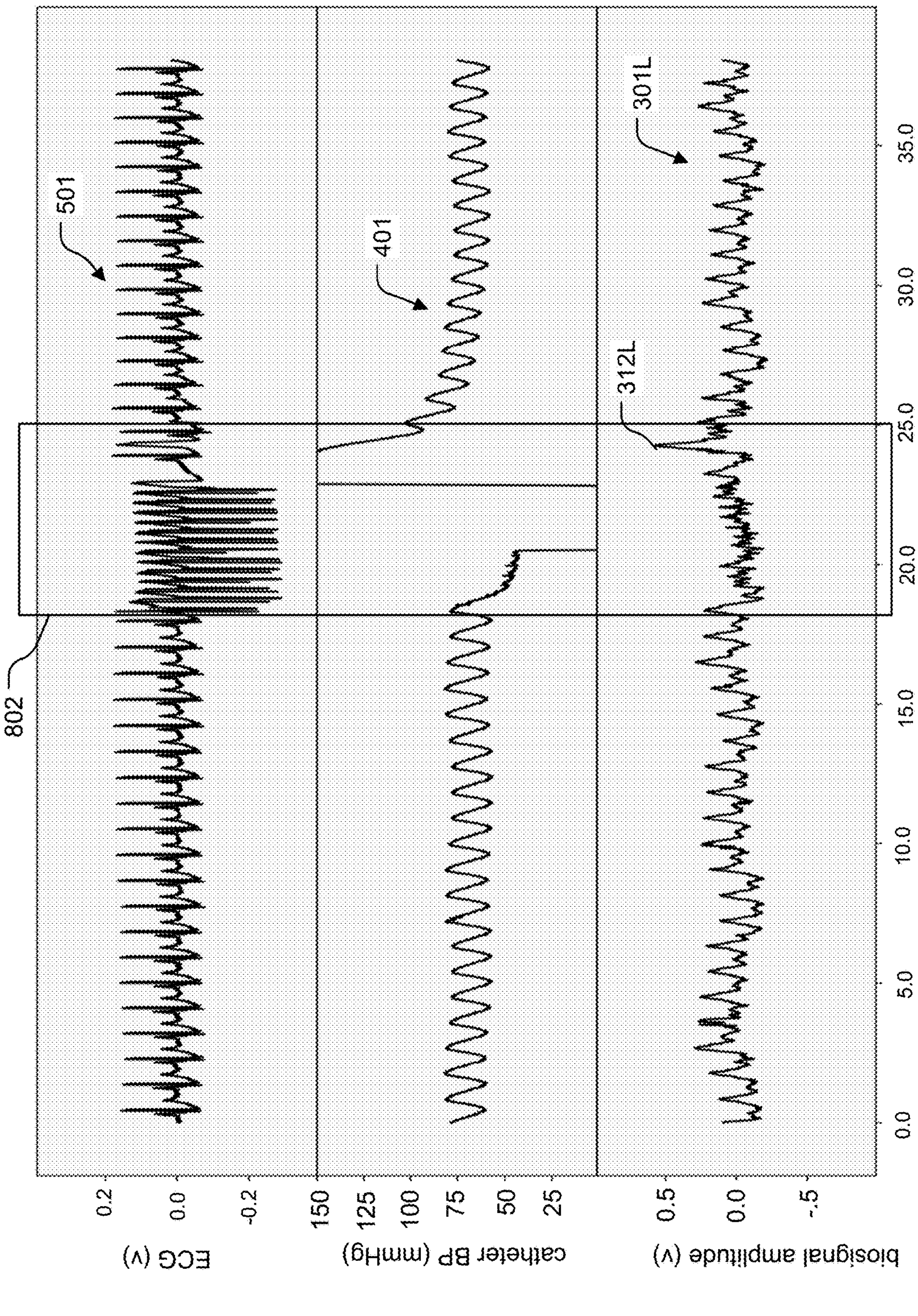
FIG. 8A-8C are plots of signals for the same individual as in FIG. 6A-6C, where the signal plots were respectively obtained by the ECG system, the aortic catheter system and the proposed CV stenosis system during balloon inflation at the moment of replacement of the aortic valve during the TAVR surgery, and where the plot of FIG. 8C shows only the portion of the cardiac signals from the left earbud of the CV stenosis system.

FIG. 8A-8C are signal plots of the same individual 100 with aortic stenosis, obtained during balloon inflation/valve replacement period during the TAVR surgery. FIG. 8A shows the ECG signal 501, FIG. 8B shows the BP signal 401, and FIG. 8C shows the cardiac signal 301L obtained from the left earbud 103L only.

Reference 802 highlights a balloon inflation/valve replacement period across the three plots. The balloon inflation/valve replacement period 802 is between approximately 18.5 sec and 25 sec in the figure.

Figures 9A, 9B, 9C, 9D, 9E:
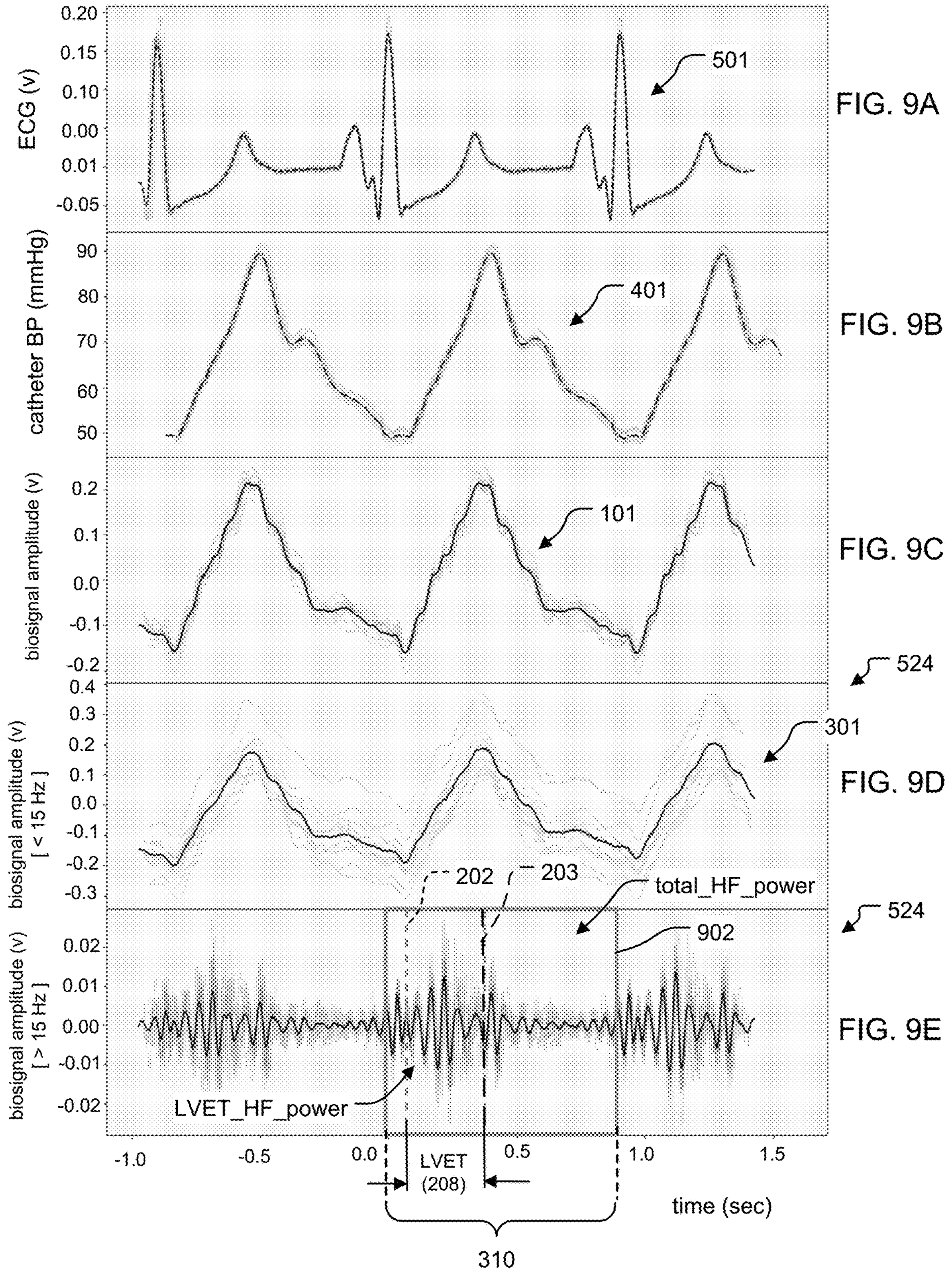
FIG. 9A-9E are signal plots obtained from an individual that illustrate operation of the method of FIG. 5B and are plotted on the same time scale, where.

FIG. 9A-9E are different signal plots of an individual 100 taken over the same time scale. FIG. 9A shows an ECG signal 501, FIG. 9B shows a BP signal 401, and FIG. 9C shows a biosignal 101 obtained by the in-ear biosensor system 102 of the CV stenosis system 10.

FIGS. 9D and 9E are signal plots that the data analysis system 109 derives or calculates from the biosignals in FIG. 9C and illustrate operation of step 526 in the method of FIG. 5A hereinabove.

FIG. 9D shows cardiac signals 301 of the biosignals 101 that have frequency values below 15 Hz. FIG. 9E, in contrast, shows components of the biosignals 101 that are greater than 15 Hz and that the data analysis system 109 has additionally performed operations upon in an effort to characterize the stenosis as left or right carotid artery stenosis. In the illustrated example, integrated versions of the components of the biosignals 101 that are greater than 15 Hz are shown and plotted over approximately three seconds.

In more detail, at least one cardiac cycle 310 of the integrated signals is shown, and the portion of the signals from which the total_HF_power value is calculated is shown within highlighted box 902. The portion of the signals from which the LVET_HF_power is calculated is also shown, which includes the signals over the LVET 208.

While this invention has been particularly shown and described with references to preferred embodiments thereof, it will be understood by those skilled in the art that various changes in form and details may be made therein without departing from the scope of the invention encompassed by the appended claims.

What is claimed is:

1. A cardiovascular (CV) stenosis monitoring, diagnosis, analysis and reporting system (CV stenosis system), the CV stenosis system comprising:

an interface configured to receive biosignals including infrasonic cardiac signals from one or more earbuds worn by an individual, wherein the one or more earbuds include sensors that detect the biosignals including the infrasonic cardiac signals in ear canals of the individual; and a data analysis system that is configured to detect and characterize an aortic cardiovascular stenosis medical condition of the individual based upon the received biosignals;

wherein the data analysis system derives a left ventricular ejection time (LVET) vital sign and a rapid ejection period (REP) vital sign from the biosignals, divides the REP by the LVET to obtain an Ejection Efficiency Ratio, and compares the Ejection Efficiency Ratio to threshold values to detect the aortic cardiovascular stenosis medical condition of the individual and characterize its severity.

2. The CV stenosis system of claim 1, wherein the data analysis system passes aspects of the cardiac signals, in conjunction with vital signs and with representations of cardiac shape, as input to one or more previously built cardiovascular stenosis models to provide a prediction and severity of aortic stenosis and a prediction of left or right carotid artery stenosis as output of the one or more models.

3. A cardiovascular (CV) stenosis monitoring, diagnosis, analysis and reporting system (CV stenosis system), the CV stenosis system comprising:

an interface configured to receive biosignals including a left infrasonic cardiac signal from a left earbud worn by an individual and a right infrasonic cardiac signal from a right earbud worn by the individual, wherein the left and right earbuds each include sensors that detect the biosignals including the left and right infrasonic cardiac signals in ear canals of the individual; and a data analysis system that is configured to detect and characterize a carotid artery cardiovascular stenosis medical condition of the individual based upon the received biosignals wherein the data analysis system calculates a left high frequency power ratio for the left cardiac signal from the left earbud and calculates a right high frequency power ratio for the right cardiac signal from the right earbud, and wherein the left high frequency power ratio relates a high frequency power calculated for a left ventricular ejection time (LVET) of the left cardiac signal during a cardiac cycle to a high frequency power calculated for the left cardiac signal over the cardiac cycle, and wherein the right high frequency power ratio relates a high frequency power calculated for an LVET of the right cardiac signal during the cardiac cycle to a high frequency power calculated for the right cardiac signal over the cardiac cycle, and wherein the data analysis system subtracts the right high frequency power ratio from the left high frequency power ratio to obtain a difference, and compares the difference to a threshold value to detect a carotid the carotid artery cardiovascular stenosis medical condition of the individual and characterize it as left carotid artery cardiovascular stenosis.

4. The CV stenosis system of claim 3, wherein the data analysis system includes a processor and a memory and is configured to subtract the left high frequency power ratio from the right high frequency power ratio to obtain a second difference, and is configured to compare the second difference to the threshold value to detect the carotid artery cardiovascular stenosis medical condition of the individual and characterize it as right carotid artery cardiovascular stenosis.

5. The CV stenosis system of claim 4, wherein the data analysis system concludes that the left carotid artery cardiovascular stenosis is present when the left high frequency power ratio exceeds a left threshold value associated with known left carotid artery cardiovascular stenosis, and concludes that the right carotid artery cardiovascular stenosis is present when the right high frequency power ratio exceeds a right threshold value associated with known right carotid artery cardiovascular stenosis.

6. A cardiovascular (CV) stenosis monitoring, diagnosis, analysis and reporting system (CV stenosis system), the CV stenosis system comprising:

an interface configured to receive biosignals including infrasonic cardiac signals from one or more earbuds worn by an individual, wherein the one or more earbuds include sensors that detect the biosignals including the infrasonic cardiac signals in ear canals of the individual; and a data analysis system that is configured to detect and characterize a cardiovascular stenosis medical condition of the individual based upon the received biosignals;

wherein the data analysis system calculates a high frequency power ratio for the cardiac signals that relates a high frequency power calculated for a ventricular diastole of the cardiac signals during a cardiac cycle to a high frequency power calculated for the cardiac cycle, and wherein the data analysis system compares the high frequency power ratio to a threshold value to detect whether aortic regurgitation is present.

7. A cardiovascular stenosis monitoring, diagnosis, analysis and reporting method, the method comprising:

receiving biosignals including infrasonic cardiac signals from one or more earbuds worn by an individual, at an interface, wherein the one or more earbuds include sensors that detect the biosignals including the infrasonic cardiac signals in ear canals of the individual;

deriving a left ventricular ejection time (LVET) vital sign and a rapid ejection period (REP) vital sign from the biosignals;

dividing the REP by the LVET to obtain an Ejection Efficiency Ratio;

comparing the Ejection Efficiency Ratio to threshold values to detect an aortic cardiovascular stenosis medical condition of the individual and characterize its severity;

recording values for the detected and characterized aortic cardiovascular stenosis medical condition of the individual to a medical record for the individual;

comparing the recorded values to reference values for each of the recorded values, and sending notification messages to the individual and to medical professionals when results of the comparisons exceed threshold levels for each of the reference values.

8. The method of claim 7, wherein detecting and characterizing cardiovascular stenosis of the individual comprises passing aspects of the cardiac signals, in conjunction with vital signs and with representations of cardiac shape, as input to one or more previously built cardiovascular stenosis models to provide a prediction and severity of aortic stenosis and a prediction of left or right carotid artery stenosis as output of the one or more models.

9. A cardiovascular stenosis monitoring, diagnosis, analysis and reporting method, the method comprising:

receiving biosignals including left infrasonic cardiac signals from a left earbud worn by an individual and right infrasonic cardiac signals from a right earbud worn by the individual, at an interface, wherein the left and right earbuds include sensors that detect the biosignals including the respective left and right infrasonic cardiac signals in ear canals of the individual;

calculating a left high frequency power ratio for a left cardiac signal from a left earbud and calculating a right high frequency power ratio for a right cardiac signal from a right earbud, the left high frequency power ratio relating a high frequency power calculated for a left ventricular ejection time (LVET) of the left cardiac signal during a cardiac cycle to a high frequency power calculated for the left cardiac signal over the cardiac cycle, and the right high frequency power ratio relating a high frequency power calculated for the L VET of the right cardiac signal during the cardiac cycle to a high frequency power calculated for the right cardiac signal over the cardiac cycle;

subtracting the right high frequency power ratio from the left high frequency power ratio to obtain a difference;

comparing the difference to a threshold value to detect a carotid artery cardiovascular stenosis medical condition of the individual and characterize it as left carotid artery cardiovascular stenosis, recording values for the detected and characterized carotid artery cardiovascular stenosis medical condition of the individual to a medical record for the individual, comparing the recorded values to reference values for each of the recorded values, and sending notification messages to the individual and to medical professionals when results of the comparisons exceed threshold levels for each of the reference values.

10. The method of claim 9, further comprising subtracting the left high frequency power ratio from the right high frequency power ratio to obtain a second difference, and comparing the second difference to the threshold value to detect the carotid artery cardiovascular stenosis medical condition of the individual and characterize it as right carotid artery cardiovascular stenosis.

11. The method of claim 10, further comprising concluding that the left carotid artery cardiovascular stenosis is present when the left high frequency power ratio exceeds a left threshold value associated with known left carotid artery cardiovascular stenosis, and concluding that the right carotid artery cardiovascular stenosis is present when the right high frequency power ratio exceeds a right threshold value associated with known right carotid artery cardiovascular stenosis.

12. A cardiovascular stenosis monitoring, diagnosis, analysis and reporting method, the method comprising:

receiving biosignals including infrasonic cardiac signals from one or more earbuds worn by an individual, at an interface, wherein the one or more earbuds include sensors that detect the biosignals including the infrasonic cardiac signals in ear canals of the individual;

detecting and characterizing a cardiovascular stenosis medical condition of the individual based upon the received biosignals;

recording values for the detected and characterized cardiovascular stenosis medical condition of the individual to a medical record for the individual, comparing the recorded values to reference values for each of the recorded values, and sending notification messages to the individual and to medical professionals when results of the comparisons exceed threshold levels for each of the reference values; and calculating a high frequency power ratio for the cardiac signals that relates a high frequency power calculated for a ventricular diastole of the cardiac signals during a cardiac cycle to a high frequency power calculated for the cardiac cycle, and comparing the high frequency power ratio to a threshold value to detect whether aortic regurgitation is present.

* * * * *